(12) United States Patent
Hart et al.

(10) Patent No.: US 12,111,209 B2
(45) Date of Patent: Oct. 8, 2024

(54) COMPACT DIFFRACTION LIMITED NEAR INFRARED (NIR) SPECTROMETERS AND RELATED DETECTORS

(71) Applicant: Leica Microsystems NC, Inc., Durham, NC (US)

(72) Inventors: Robert H. Hart, Cary, NC (US); Peter Strobel, Eggersriet (CH)

(73) Assignee: LEICA MICROSYSTEMS NC, INC., Durham, NC (US)

( * ) Notice: Subject to any disclaimer, the term of this patent is extended or adjusted under 35 U.S.C. 154(b) by 0 days.

(21) Appl. No.: 17/296,282

(22) PCT Filed: Nov. 22, 2019

(86) PCT No.: PCT/US2019/062737
§ 371 (c)(1),
(2) Date: May 24, 2021

(87) PCT Pub. No.: WO2020/112521
PCT Pub. Date: Jun. 4, 2020

(65) Prior Publication Data
US 2022/0018712 A1    Jan. 20, 2022

Related U.S. Application Data

(60) Provisional application No. 62/772,754, filed on Nov. 29, 2018.

(51) Int. Cl.
*G01J 3/02* (2006.01)
*G01B 9/02* (2022.01)
(Continued)

(52) U.S. Cl.
CPC ........ *G01J 3/0291* (2013.01); *G01B 9/02044* (2013.01); *G01B 9/02091* (2013.01);
(Continued)

(58) Field of Classification Search
CPC ...... G01J 3/0291; G01J 3/0208; G01J 3/0221; G01J 3/0256; G01J 3/0272; G01J 3/0286;
(Continued)

(56) References Cited

U.S. PATENT DOCUMENTS

| 1,682,572 A  * | 8/1928 | Keuffel | G01J 3/28 |
| | | | 356/232 |
| 2004/0075058 A1* | 4/2004 | Blevis | G01T 1/1642 |
| | | | 250/370.09 |

(Continued)

FOREIGN PATENT DOCUMENTS

| CN | 1681432 A | 10/2005 |
| CN | 103017902 A | 4/2013 |

(Continued)

OTHER PUBLICATIONS

Office Action issued by the Japanese Patent Office on Jul. 26, 2022, in Patent Application JP2021530992A, published Nov. 18, 2021.
(Continued)

*Primary Examiner* — Tarifur R Chowdhury
*Assistant Examiner* — Kemaya Nguyen
(74) *Attorney, Agent, or Firm* — LEYDIG, VOIT & MAYER, LTD.

(57) ABSTRACT

Spectrometer systems are provided including a detector array; an imaging lens assembly coupled to the detector array, the imaging lens assembly including a first element of positive optical power followed by a second element of negative optical power and a positive optical power element split into two opposing identical singlets; a dispersive element coupled to the imaging lens assembly; and a fixed focus collimator assembly coupled to the dispersive element. Related imaging lens assemblies and collimator assemblies are also provided.

10 Claims, 6 Drawing Sheets

(51) Int. Cl.
*G01B 9/02091* (2022.01)
*G01J 3/28* (2006.01)
*G01J 3/45* (2006.01)
*G02B 9/10* (2006.01)
*G02B 27/30* (2006.01)

(52) U.S. Cl.
CPC ........... *G01J 3/0208* (2013.01); *G01J 3/0221* (2013.01); *G01J 3/0256* (2013.01); *G01J 3/0272* (2013.01); *G01J 3/0286* (2013.01); *G01J 3/2803* (2013.01); *G01J 3/45* (2013.01); *G02B 9/10* (2013.01); *G02B 27/30* (2013.01)

(58) Field of Classification Search
CPC ...... G01J 3/2803; G01J 3/45; G01B 9/02044; G01B 9/02091; G02B 9/10; G02B 27/30
See application file for complete search history.

(56) References Cited

U.S. PATENT DOCUMENTS

| | | |
|---|---|---|
| 2005/0242298 A1 | 11/2005 | Genet et al. |
| 2006/0158655 A1 | 7/2006 | Everett et al. |
| 2007/0030483 A1* | 2/2007 | Everett .............. G01B 9/02091 356/328 |
| 2010/0014081 A1 | 1/2010 | Huening et al. |
| 2012/0242988 A1* | 9/2012 | Saxer ........................ G01J 3/28 356/326 |
| 2012/0262720 A1 | 10/2012 | Brown et al. |
| 2014/0346230 A1 | 11/2014 | Liu et al. |
| 2015/0331225 A1* | 11/2015 | Huang ............... G02B 13/0045 359/713 |
| 2016/0041033 A1 | 2/2016 | Oskotsky et al. |
| 2017/0311797 A1 | 11/2017 | Kuo et al. |

FOREIGN PATENT DOCUMENTS

| | | |
|---|---|---|
| CN | 106918894 A | 7/2017 |
| EP | 0163362 A1 | 12/1985 |
| JP | H01309014 A | 12/1989 |
| JP | H08145794 A | 6/1996 |
| JP | 2004191244 A | 7/2004 |
| JP | 2009128607 A | 6/2009 |
| JP | 2010035949 A | 2/2010 |
| JP | 2016197169 A | 11/2016 |

OTHER PUBLICATIONS

Betters et al., "Demonstration and design of a compact diffraction limited spectrograph," Proceeding of SPIE, vol. 8446, Sep. 24, 2012, p. 84463H.
Chuang et al., "Design of a aberration-corrected VIS-NIR imaging spectrograph," Optics Communications, vol. 272, No. 2, Feb. 24, 2007, pp. 330-335.
Sharma, K.D., "Four-element lens systems of the Cooke Triplet family: designs," Applied Optics, vol. 19, No. 5, Mar. 1, 1980, p. 698.
Notification of Transmittal of the International Search Report and Written Opinion of the International Searching Authority, PCT/US2019/062737, May 4, 2020, 21 pages.
Hu et al. "Optical design of refracting collimator with large aperture and wide spectrum" Chinese Journal of Quantum Electronics DOI: 10.3969/j.issn.1007-5461.2013.05.004vol. 30, No. 5; Sep. 2013.
Huang et al. "Optical design of wide bands and long focal length collimating lens" vol. 36 Supplement Infrared and Laser Engineering Sep. 2007.
Zhai et al. "Design of underwater zoom lens" 1002-2082(2007) 04-0416-05.

* cited by examiner

COMPACT DIFFRACTION LIMITED NEAR INFRARED (NIR) SPECTROMETERS AND RELATED DETECTORS

CROSS-REFERENCE TO RELATED APPLICATIONS

The present application is a U.S.C. § 371 national phase application of PCT International Application No. PCT/US2019/062737, filed Nov. 22, 2019, which claims priority to U.S. Provisional Patent Application No. 62/772,754, filed Nov. 29, 2018. The disclosures of each are hereby incorporated herein by reference in their entireties.

FIELD

The present inventive concept relates to imaging and, more particularly, to Spectral Domain optical coherence tomography (SDOCT) systems and related devices.

BACKGROUND

Optical coherence tomography (OCT) is a noninvasive imaging technique that provides microscopic tomographic sectioning of biological samples by acquiring the interferometric signal generated by mixing sample light with reference light at a fixed group delay as a function of optical wavenumber. Two distinct methods have been developed which use this Fourier domain OCT (FD-OCT) approach. The first, generally termed Spectral-domain or spectrometer based OCT (SDOCT), uses a broadband light source and achieves spectral discrimination with a dispersive spectrometer in the detector arm. The second, generally termed swept-source OCT (SSOCT) or optical frequency-domain imaging (OFDI), time-encodes wavenumber by rapidly tuning a narrowband source through a broad optical bandwidth.

Spectrometer based implementations of FDOCT have the potential advantage of phase stability, as the source and detection modules are passive. However, in practice spectrometer based designs for high resolution imaging have been shown to have some shortcomings. High resolution spectrometers rely on a highly dispersive element with optics that provide approximately constant magnification imaging across a broad focal plane. Optical designs using transmission volume phase holograms or reflective Echelle gratings for achieving desired results are well known and applied in many laboratory set-ups.

However, manufacturers have found it difficult to develop a spectrometer that is relatively easy to manufacture and passively stable in the face of environmental perturbation. A proposed solution to the environmental stability issue is discussed in U.S. Pat. No. 7,480,058 entitled Fourier-domain Optical Coherence Tomography Imager to Wei et al, the content of which is hereby incorporated herein by reference as if set forth in its entirety. The system discussed therein has the capability to continually adjust alignment to optimize attributes of the spectrograph using an actively controlled fold mirror.

SUMMARY

Some embodiments of the present inventive concept provide spectrometer systems including a detector array; an imaging lens assembly coupled to the detector array, the imaging lens assembly including a first element of positive optical power followed by a second element of negative optical power and a positive optical power element split into two opposing identical singlets; a dispersive element coupled to the imaging lens assembly; and a fixed focus collimator assembly coupled to the dispersive element.

In further embodiments, the system may further include a lens cell housing and the imaging lens assembly may be positioned in the lens cell housing.

In still further embodiments, the system may further include a spectrometer housing made of material having a low thermal coefficient of expansion. The imaging lens assembly may be positioned in the spectrometer housing.

In some embodiments, the second element of negative optical power may also function as a field stop.

In further embodiments, the dispersive element may be a diffraction grating; the fixed focus collimator assembly may include a single piece of material having a low thermal coefficient of expansion; and the single piece of material may provide both a grating mounting feature for the diffraction grating and a collimating lens mounting feature for a collimating lens assembly.

In still further embodiments, the collimating lens assembly may include a first negative optical power element followed by a second positive optical power element providing collimated light from an optical radiation input fiber to the diffraction grating held at a fixed angle relative to the collimated light.

In some embodiments, the single piece of material may further include a mounting feature for an input fiber and the fixed focus collimator assembly may be fixed to a spectrometer housing. The spectrometer housing may be machined from a single piece of a same low thermal coefficient of expansion material as the fixed focus collimator assembly.

In further embodiments, wavelength dispersed optical radiation may be normal incident on the detector array with an overall optical path length of less than 225 mm.

In still further embodiments, the spectrometer system may be a compact diffraction limited near infrared (NIR) spectrometer.

In some embodiments, the system may have a 10 um detector pixel width and short 223 mm optical path length.

Further embodiments of the present inventive concept provide an imaging lens assembly for use in a near infrared (NIR) spectrometer. The imaging lens assembly includes a first element of positive optical power; a second element of negative optical power; and a positive optical power element split into two opposing identical singlets, wherein the first element is followed by the second element and then the positive optical power element.

Still further embodiments of the present inventive concept provide a fixed focus collimator assembly for use in a near infrared spectrometer. The fixed focus collimator assembly includes a single piece of material having a low thermal coefficient of expansion, wherein the single piece of material provides both a grating mounting feature for a diffraction grating of the spectrometer and a collimating lens mounting feature for a collimating lens assembly.

DETAILED DESCRIPTION

Figure 1:
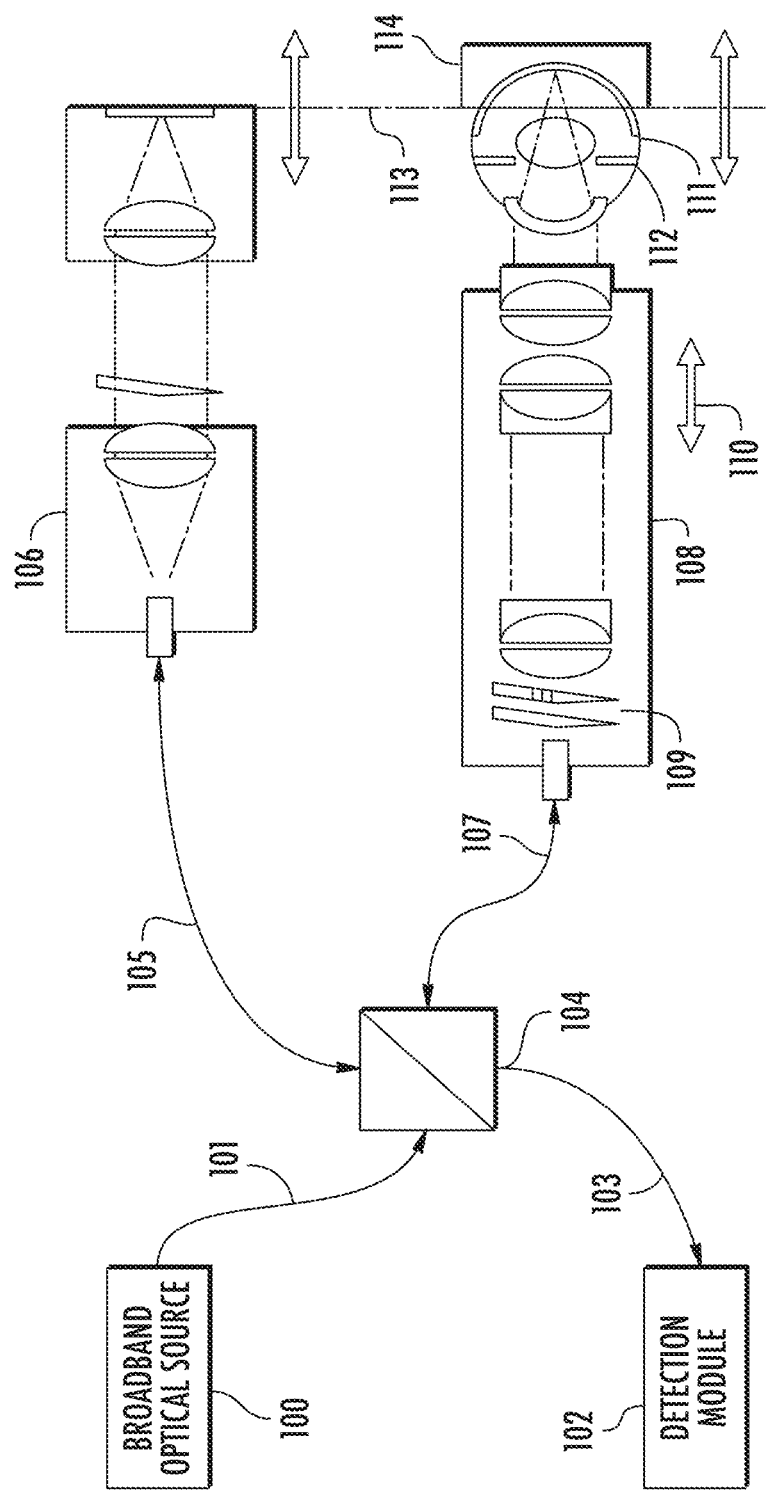
FIG. 1 is a diagram illustrating a conventional ophthalmic Fourier domain optical coherence tomography (OCT) system.

The present inventive concept will be described more fully hereinafter with reference to the accompanying figures, in which embodiments of the inventive concept are shown. This inventive concept may, however, be embodied in many alternate forms and should not be construed as limited to the embodiments set forth herein.

Accordingly, while the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept as defined by the claims. Like numbers refer to like elements throughout the description of the figures.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this inventive concept belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

As discussed in the background of the present application, although spectrometer based implementations offer many advantages, improvement of these implementations is still desired. For example, as discussed above, a need for a spectrometer that is relatively easy to manufacture and passively stable in the face of environmental perturbation is desired. A solution that has both a mechanically stable optical design coupled with a rigidly fixed detector array will be discussed in accordance with some embodiments herein.

For best OCT imaging performance, to achieve a high sensitivity and low signal fall-off over the imaging depth a spectrometer should be designed with diffraction limited optical performance. The combination of diffraction limited imaging and a small detector size presents a very difficult mechanical stability problem for the spectrometer, often resulting in image quality degradation over time. This problem is particularly prevalent in mobile imaging systems. For example, handheld OCT produced by Bioptigen is the first compact system for ophthalmic imaging of pediatric, confined, or infirm patients that does not require the patient to sit a tabletop instrument as discussed in commonly assigned U.S. Pat. No. 8,421,855, the content of which is hereby incorporated herein by reference as if set forth in its entirety.

As will be discussed further herein with respect to FIGS. 1 through 6F, some embodiments of the present inventive concept provide a spectrometer that achieves the required optical performance for the best OCT image and long-term alignment stability resulting in improved over all system quality.

In particular, existing spectrometers are designed based on a dual row 2048-pixel linear array with 14 um pixel size, which generally results in a total pixel height of 28 um in which the spectrometer image is aligned and must stay in alignment through transport, continued use and frequent relocation, for example, between operating rooms, over the lifetime of the spectrometer. This creates a very difficult mechanical requirement for alignment stability, which can result in quality issues. Existing spectrometers use a long focal length, non-diffraction limited optical design to over fill the detector in order to relieve some of the mechanical alignment burden, but there is a performance trade-off. The result is an optical path length of 375 mm, which is still susceptible to alignment errors over time and frequent system relocation. Furthermore, conventional table top design systems are not easily moved from place to place (i.e. are not mobile) and as such make them unsuitable for the targeted OCT market.

New detector technology allows for relaxed mechanical constraints on the optical alignment of the spectrometer by offering pixels with a 7× advantage in pixel height, but with a 0.7× pixel width. The reduced pixel width results in a reduced optical image width. Thus, to properly take advantage of the new detector design and achieve the highest optical performance for the OCT system spectrometer, embodiments of the present inventive concept provide a diffraction limited design.

In particular, embodiments of the present inventive concept provide a true diffraction limited design based on a 10 um detector pixel width and short 223 mm optical path length for greater mechanical stability. As will be discussed below, in some embodiments of the present inventive concept, the optical design consists of an air spaced achromatic collimator having an integral diffraction grating for improved pointing stability and an air spaced triplet form factor imaging lens assembly with split positive elements as will be discussed further below with respect to FIGS. 1 through 6F.

Although the examples provided herein refer to 100 nm bandwidth spectrometers, it will be understood that embodiments of the present inventive concept are not limited to this configuration. As will be understood by those of skill in the art, aspects of the present inventive concept may be used with various spectrometers without departing from the scope of the present inventive concept. Furthermore, although embodiments of the present inventive concept are discussed herein with respect the NIR spectrum, embodiments of the present inventive concept are not limited thereto. Other regions of the electromagnetic spectrum may be addressed without departing from the scope of the present inventive concept.

As used herein, "optical path length" refers to the physical path traveled by light inclusive of the index of refraction for the non-air optical elements; "focal length" refers to the distance from a lens surface to the point where a marginal ray crosses the optical axis of the lens; "axial color shift" refers to the change in focal length relative to the wavelength of light; and "Petzval field curvature" refers to the change in focal length of a lens or lens assembly relative to the field position tangential to the optical axis of the lens or lens assembly.

Referring first to FIG. 1, a block diagram illustrating a conventional Fourier domain optical coherence tomography (FDOCT) ophthalmic imaging system will be discussed. As illustrated in FIG. 1, the system includes a broadband optical source 100 directed along a source path 101 to a beamsplitter 104, where the source radiation is divided into a reference path 105 and a sample path 107. The reference light is returned through a reference reflection device 106 back through the beamsplitter 104 where it mixes with the light returned from a sample, such as the retina of an eye 111. The resultant wavelength dependent interferogram is directed through a detection path 103 to a detection module 102. The total spectral interferogram is processed using Fourier transforms to derive a spatial domain depth resolved image.

In contrast to a time domain OCT system, where the reference mirror scans a range over time that matches the depth range of interest for image the subject to acquire a temporal interferogram, the FDOCT system acquires a spectral interferogram from a fixed reference position 113 that is path length matched to a target axial position with respect to the subject. The spectral interferogram contains information for all depths within a window 114. The window is defined by parameters of detection as is known in the art. A scanning subsystem 108 includes a pair of scanning galvo mirrors 109 and an objective lens set with focal capabilities 110. For posterior, or retinal, ophthalmic imaging, the scanned OCT beam is directed through the pupil of the eye 112 to image the retina. An FDOCT system may include a serial acquisition of spectral information using a broadband swept frequency optical source, or a parallel acquisition of spectral information using a broadband low coherence source and a spectrometer, or a combination of these methods. A spectrometer based system is referred to as spectral domain optical coherence tomography (SDOCT) and a swept source system is referred to swept source OCT (SSOCT).

Figure 2:
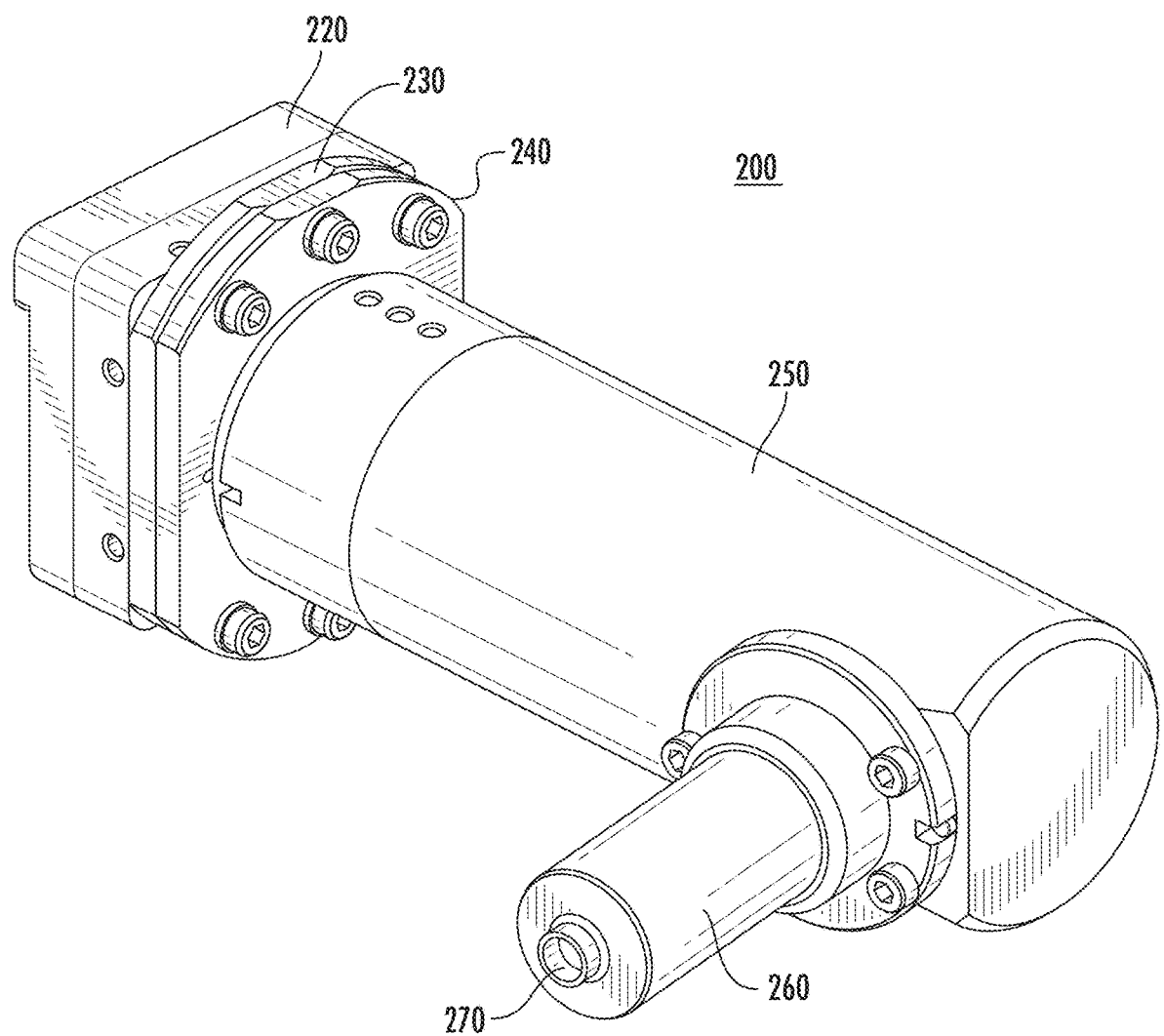
FIG. 2 is a diagram illustrating an isometric view of the compact Near Infrared (NIR) Spectrometer in accordance with some embodiments of the present inventive concept.

Embodiments of the present inventive concept are directed to spectrometer based systems. Referring now to FIG. 2, a diagram illustrating an isometric view of the compact Near Infrared (NIR) Spectrometer in accordance with some embodiments of the present inventive concept will be discussed. As illustrated in FIG. 2, the spectrometer system 200 includes a detector array 220, a detector array interface 230, a detector array mount 240, a spectrometer body 250, a fixed focus collimator assembly 260 and an optical radiation input fiber connector 270.

The detector array interface 230 provides for linear adjustment in the sagittal direction relative to the optical axis. The detector array mount 240 provides rotational adjustment about the optical axis and translation along the optical axis for focus adjustment. Furthermore, the fixed focus collimator assembly 260 is a single piece of material that provides both a grating mounting feature and a collimating lens mounting feature. In some embodiments, the single piece of material is a low thermal coefficient of expansion material, such as stainless steel. However, embodiments of the present inventive concept are not limited to materials having low thermal coefficients of expansion.

Thermal expansion generally refers to a fractional change in size of a material in response to a change in temperature. A thermal coefficient of expansion is the ratio of an increase of length, area, or volume of a body of material per degree rise in temperature to its length, area, or volume, respectively, at some specified temperature, commonly 0° C., the pressure being kept constant. For materials used in some embodiments of the present inventive concept, a coefficient of no greater than 20 µm/m-° C. for linear expansion between temperatures of 0 to 100° C. is acceptable. Thus, although stainless steel is provided as an example material, embodiments of the present inventive concept are not limited thereto. Materials having various coefficients of expansion may be used without departing from the scope of the present inventive concept.

Figure 3:
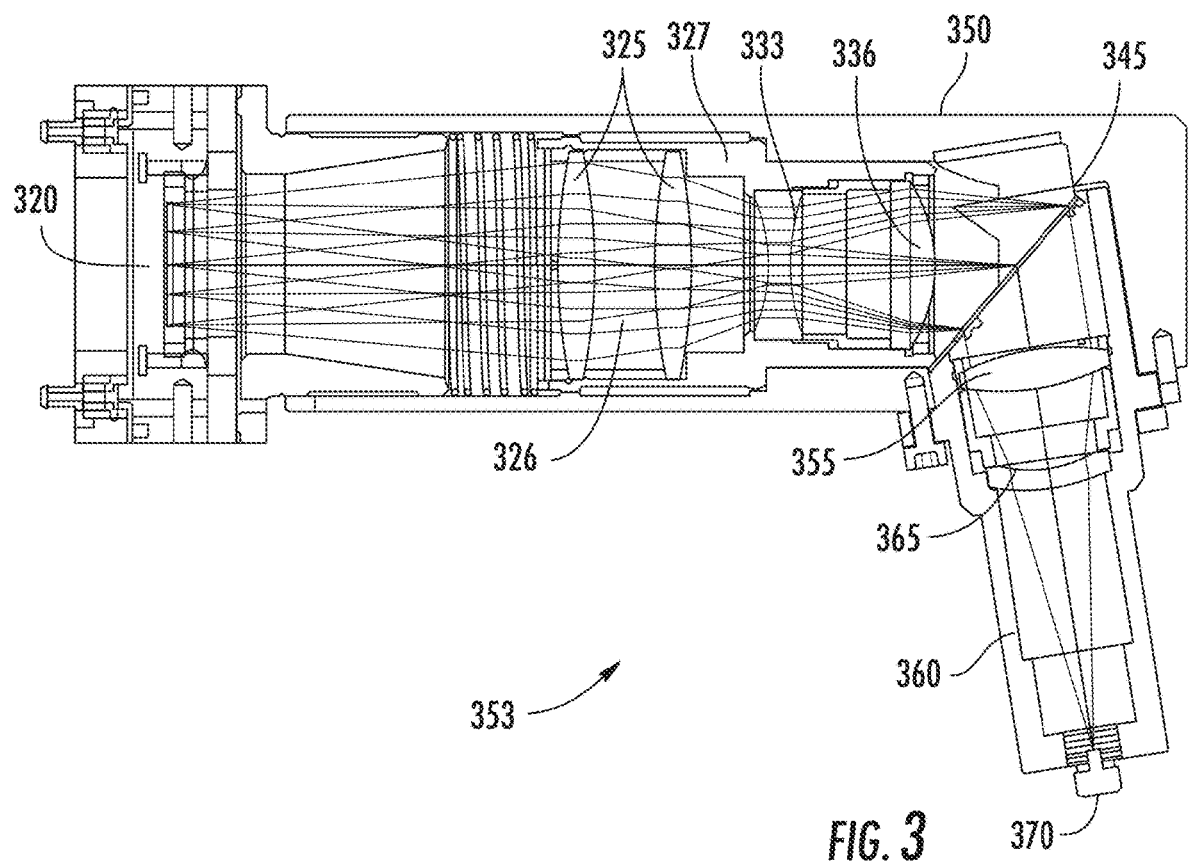
FIG. 3 is a diagram illustrating a cut away view of the compact NIR Spectrometer in accordance with some embodiments of the present inventive concept.

FIG. 3 is a cut away view of the compact NIR Spectrometer of FIG. 2 in accordance with some embodiments of the present invention. FIG. 3 illustrates a different view of many of the elements illustrated in FIG. 2 as well as details associated with the elements of FIG. 2 and additional elements of FIG. 3. As illustrated in FIG. 3, the system includes a detector array 320, an imaging lens assembly 327, a spectrometer body 350, a diffraction grating 345, and a collimating lens positive lens element 355, a collimating lens negative lens element 365, a fixed focus collimator assembly 360 and a fiber input connector 370.

The imaging lens assembly 327 includes a first element of positive optical power 336 followed by a second element of negative optical power 333 also functioning as a field stop and a final positive optical power element split into two opposing identical singlets 325 housed in a lens cell 326, for example, a brass lens cell. It will be understood that although the singlets are described herein as identical, a small amount of variation is acceptable without departing from the scope of the present inventive concept. The imaging lens assembly 327 is housed within spectrometer body 350 made of, for example, stainless steel, which also acts as the receptacle for the collimating lens assembly. The collimating lens assembly includes a first negative optical power element 365 followed by a second positive optical power element 355 providing collimated light from the optical radiation input fiber connector 370 to the diffraction grating 345 held at a fixed angle relative to the collimated light. The first negative optical power element 365 and the second positive optical power element 355 define the collimating lens assembly 353 indicated by the arrow. It will be understood that materials such as brass and stainless steel are provided as examples only, embodiments of the present inventive concept are not limited to this configuration. Other materials providing similar results may also be used without departing from the scope of the present inventive concept.

Figure 4:
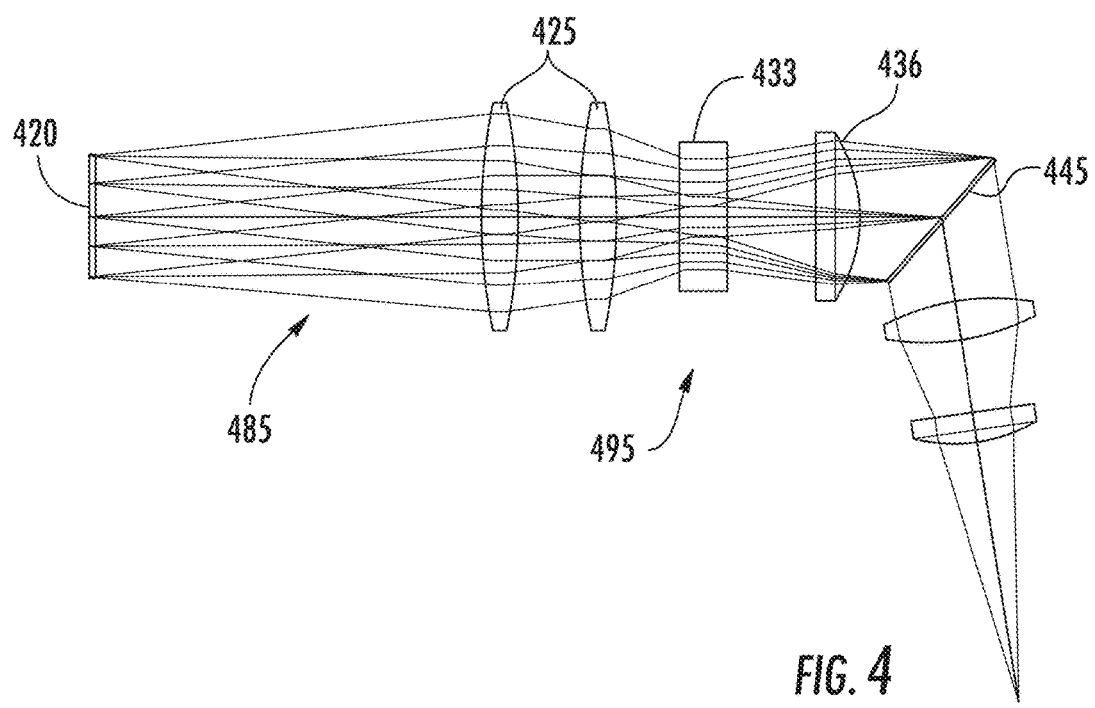
FIG. 4 is a diagram illustrating an optical layout for compact NIR Spectrometer, 100 nm Bandwidth in accordance with some embodiments of the present inventive concept.

FIG. 4 is a diagram illustrating an optical layout for compact NIR Spectrometer, 100 nm Bandwidth in accordance with some embodiments of the present invention. As discussed above, although embodiments of the present inventive concept discuss spectrometers having a 100 nm bandwidth, embodiments of the present inventive concept are not limited to this configuration. As illustrated in FIG. 4, the optical layout includes, but is not limited to, a detector array 420, a split positive optical element 425, a combination negative optical element and field stop 433, a positive optical element 436 and a diffraction grating 445. The split positive optical element 425, the combination negative optical element and field stop 433, and the positive optical element 436 make up the Cooke triplet variant lens indicated by an arrow 495. The optical layout of FIG. 4 illustrates a layout in accordance with some embodiments for compact NIR Spectrometer, 100 nm Bandwidth, where the wavelength dispersed optical radiation 485 is normal incident on the detector array 420 with an overall optical path length of less than 225 mm. As used herein, "normal" indicates perpendicular.

Figure 5:
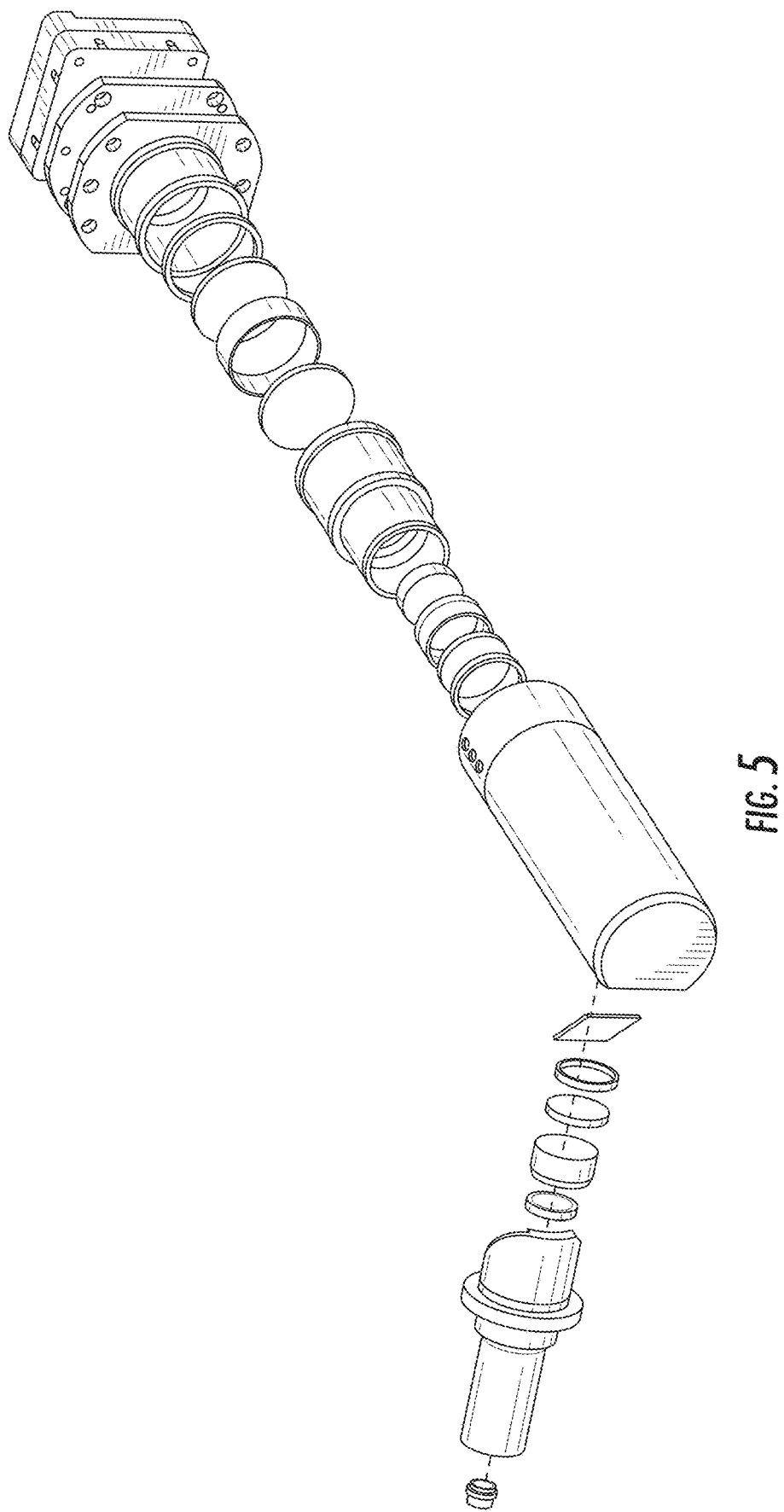
FIG. 5 is a diagram illustrating an opto-mechanical Design of the compact NIR Spectrometer, 100 nm Bandwidth in accordance with some embodiments of the present inventive concept.

FIG. 5 is a diagram illustrating the deconstructed opto-mechanical layout of the compact NIR Spectrometer, 100 nm Bandwidth discussed above with respect to FIGS. 2 through 4 in accordance with some embodiments of the present invention.

Figure 6A:
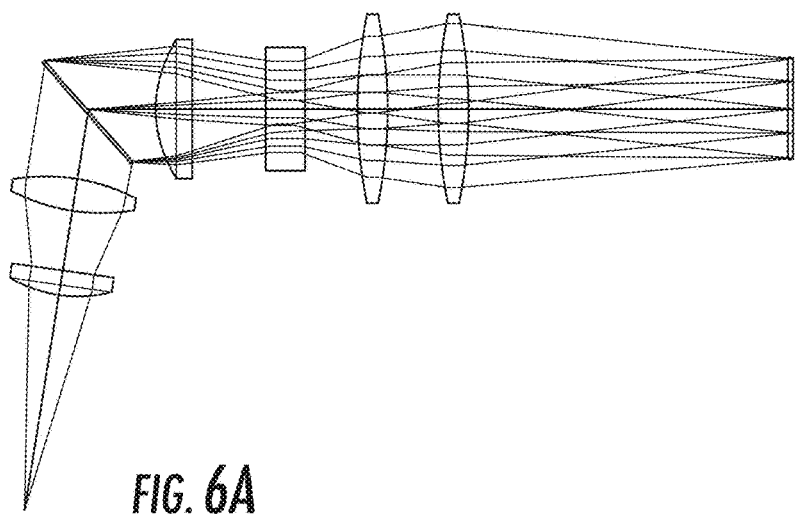
FIG. 6A is a diagram illustrating a ray trace in accordance with some embodiments of the present inventive concept.
Figure 6B:
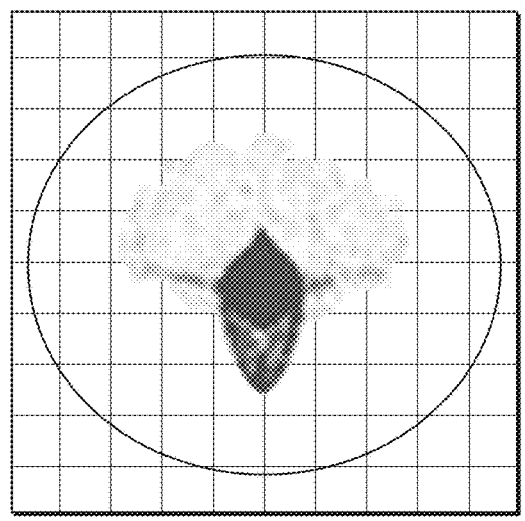
FIGS. 6B through 6F are spot diagrams showing the diffraction limited performance as defined by all the rays within the Airy disk diameter in accordance with some embodiments of the present inventive concept.
Figure 6C:
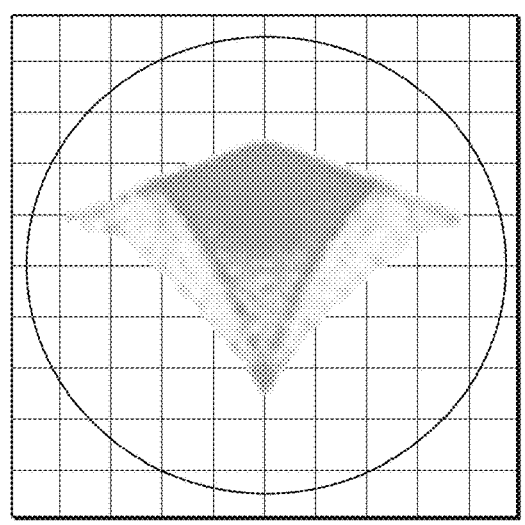

FIG. 6A is a ray trace for the optical design in accordance with embodiments discussed herein. FIG. 6A is similar to the ray trace of FIG. 4 but is positioned in the opposite direction.

Figure 6D:
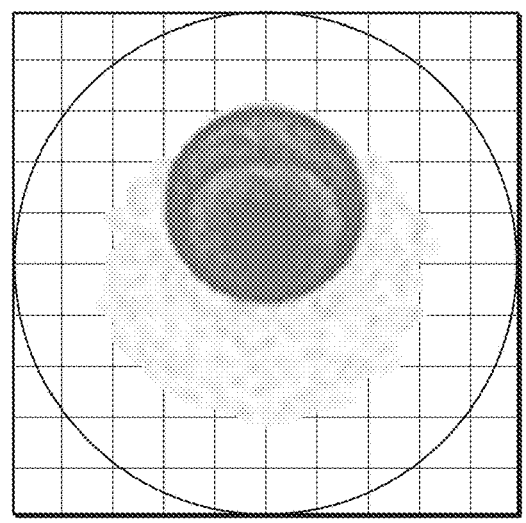
Figure 6E:
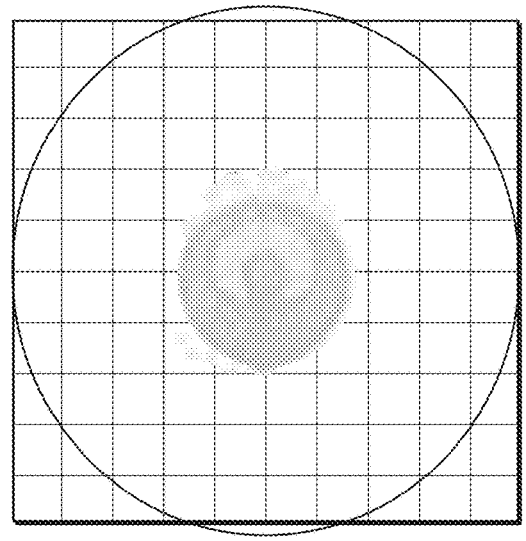
Figure 6F:
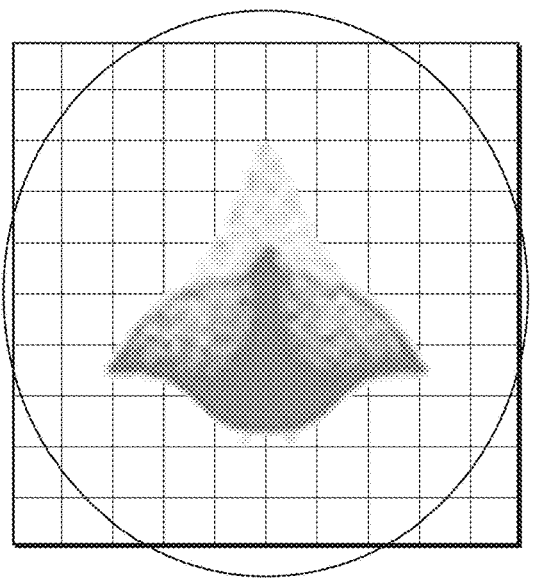

FIGS. 6B through 6F are spot diagrams showing the diffraction limited performance as defined by all the rays within the Airy disk diameter in accordance with some embodiments of the present inventive concept. FIG. 6D illustrates a spot diagram for a central wavelength in the bandwidth, which in these embodiments is also the chief ray. FIGS. 6A through 6F are provided for illustration only and, therefore, embodiments of the present inventive concept are not limited thereto.

As discussed above with respect to FIGS. 2 through 6F, embodiments of the present inventive concept are directed to spectrometer based systems that provide an environmentally stable, passively aligned spectrometer providing wavelength dispersion in the, but not limited to, near infrared (NIR) region of the electromagnetic spectrum. Environmental stability over a wide range of thermal, shock and vibration requirements is obtained using as design in accordance with embodiments discussed herein. In particular, the system design includes a short overall optical path length originating from the input radiation fiber 270, 370 and ending with the wavelength dispersed image of the input radiation fiber 270, 370 at the surface of the array detector 220, 320, 420. This may be achieved through the use of a fixed focus air spaced doublet collimating lens (FIG. 3) allowing for the first optical element 365 having negative power to effectively increase the numerical aperture of the input fiber 370 followed by a second positive optical element 355 to collimate the light from the input fiber 370 resulting in a shortened focal length collimator. The collimated beam is then projected onto a dispersive element, which in some embodiments is a transmissive diffraction grating 345.

In some embodiments, the rigidity of the fixed focus collimator assembly 260, 360 is accomplished by having the grating mounting feature and the collimating lens mounting feature machined from a single piece of low thermal coefficient of expansion material, such as stainless steel. This single machined part 260 (fixed focus collimator assembly) also includes a mounting feature for the input fiber. The fixed focus collimator assembly 260, 360 is then fixed to the body of the spectrometer 250, 350 also machined from a single piece of the same low thermal coefficient of expansion material to maintain mechanical integrity over large environmental temperature ranges. The imaging lens assembly 327 is also designed in such a way as to provide a reduced focal length to form the dispersed 100 nm optical radiation input bandwidth 485 across the face of the detector 220, 320, 420. By using a Cooke triplet design 495 (425, 435 and 441) having the first optical element 436 provide positive optical power in combination with a negative optical power center element 433 also functioning as the system field stop and splitting the second positive optical element in to two identical singlet lenses 425, both the axial color shift and Petzval field curvature are reduced producing a flat focal plane incident on the detector surface normal to the optical axis of the imaging lens assembly 327. In some embodiments, the optical design of the imaging lens assembly 327 also has a depth of focus greater than the coefficient of thermal expansion for the spectrometer body 250, 350 in the axial direction, thus maintaining focus over large temperature ranges.

As discussed above, although embodiments of the present inventive concept are discussed with respect to materials having a low coefficient of thermal expansion, embodiments of the present inventive concept are not limited thereto. Materials having various coefficients of expansion may be used without departing from the scope of the present inventive concept.

The detector mount opto-mechanical design discussed in accordance with embodiments herein allows for the linear adjustment of the detector in the cross-dispersion direction, i.e. sagittal to the optical axis. Furthermore, the detector mount 240 allows for rotational adjustment about the optical axis as well as focus along the optical axis.

The optical design in accordance with embodiments discussed herein may also afford diffraction limited optical performance, such that all the wavelength dispersed rays from the input fiber through the diffraction grating are focused to a height equivalent to the detector array element width, which in some embodiments is 10 microns. It will be understood that the design criteria discussed herein has been selected for the specific detector array in these embodiments and, thus, allows the highest theoretical resolution limit to be achieved.

As briefly discussed above, some embodiments of present inventive concept provide a spectrometer systems including, a short focal length collimator; an air spaced doublet collimator optical design to reduce the overall focal length of collimating lens; a reduced overall optical path length that reduces mechanical sensitivity; a fixed collimator to grating angle; a common mount for input fiber collimating lens and grating; a fixed grating to detector angle; a short focal length Apochromatic Cooke triplet variant imaging lens to balance axial color and Petzval curvature without image plane tilt; a detector array interface 230 (FIG. 2) providing linear adjustment in the cross-dispersion direction; a detector array mount 240 (FIG. 2) providing focus adjustment and rotational adjustment about the optical axis.

It will be understood that some methods of environmentally stabilized spectrometers come not from adequate opto-mechanical design, but through the use of detector arrays featuring large vertical height pixels in order to relax some of the alignment constraints. It should be noted that such detector array types may also be used in conjunction with the optical and opto-mechanical features discussed with respect to embodiments of the present inventive concept.

In the drawings and specification, there have been disclosed exemplary embodiments of the inventive concept. However, many variations and modifications can be made to these embodiments without substantially departing from the principles of the present inventive concept. Accordingly, although specific terms are used, they are used in a generic and descriptive sense only and not for purposes of limitation, the scope of the inventive concept being defined by the following claims.

That which is claimed is:

1. A spectrometer system comprising:
   a detector array;
   an imaging lens assembly coupled to the detector array, the imaging lens assembly including a first element of positive optical power followed by a second element of negative optical power and a positive optical power element split into two opposing identical singlets;
   a dispersive element coupled to the imaging lens assembly; and
   a fixed focus collimator assembly coupled to the dispersive element, wherein the dispersive element and the fixed focus collimator are integrated together as a rigid piece such that the rigid piece is non-adjustable in all dimensions, wherein the dispersive element is positioned between a positive element of the fixed focus collimator assembly and the first element of positive optical power of the imaging lens assembly, and wherein a fiber of the collimator is fixed and non-adjustable.

2. The spectrometer system of claim 1, further comprising a cell housing and wherein the imaging lens assembly is positioned in the cell housing.

3. The spectrometer system of claim 1, further comprising a spectrometer housing made of material having a low thermal coefficient of expansion, wherein the imaging lens assembly is positioned in the spectrometer housing.

4. The spectrometer system of claim 1, wherein the second element of negative optical power also functions as a field stop.

5. The spectrometer system of claim 1:
   wherein the dispersive element is a diffraction grating;
   wherein the fixed focus collimator assembly comprises a single piece of material having a low thermal coefficient of expansion; and
   wherein the single piece of material provides both a grating mounting feature for the diffraction grating and a collimating lens mounting feature for a collimating lens assembly.

6. The spectrometer system of claim 5, wherein the collimating lens assembly includes a first negative optical power element followed by a second positive optical power element providing fixed focus collimated light from an optical radiation input fiber to the diffraction grating held at a fixed angle relative to the collimated light.

7. The spectrometer system of claim 5, wherein the single piece of material further comprises a fixed mounting feature for an input fiber; and wherein the fixed focus collimator assembly is fixed to a spectrometer housing, the spectrometer housing being machined from a single piece of a same low thermal coefficient of expansion material as the fixed focus collimator assembly.

8. The spectrometer system of claim 5, wherein wavelength dispersed optical radiation is normal incident on the detector array with an overall optical path length of less than 225 mm.

9. The spectrometer system of claim 5, wherein the spectrometer system comprises a compact diffraction limited near infrared (NIR) spectrometer.

10. The spectrometer system of claim 5, wherein the spectrometer system has a 10 um detector pixel width and short 223 mm optical path length.

* * * * *